United States Patent
Gers-Barlag et al.

(10) Patent No.: US 6,838,088 B2
(45) Date of Patent: Jan. 4, 2005

(54) EMULSIFIER-FREE FINELY DISPERSE SYSTEMS OF THE OIL-IN-WATER- AND WATER-IN-OIL- TYPE

(75) Inventors: Heinrich Gers-Barlag, Kummerfeld (DE); Anja Müller, Rümpel (DE)

(73) Assignee: Beiersdorf AG, Hamburg (DE)

( * ) Notice: Subject to any disclaimer, the term of this patent is extended or adjusted under 35 U.S.C. 154(b) by 207 days.

(21) Appl. No.: 10/081,779

(22) Filed: Feb. 21, 2002

(65) Prior Publication Data

US 2002/0146443 A1 Oct. 10, 2002

Related U.S. Application Data

(62) Division of application No. 09/396,560, filed on Sep. 15, 1999, now Pat. No. 6,709,662.

(30) Foreign Application Priority Data

Sep. 18, 1998 (DE) .......................................... 198 42 744

(51) Int. Cl.⁷ ............................ A61K 6/00; A61K 7/00; A61K 7/42; B01F 17/00
(52) U.S. Cl. ........................ 424/401; 424/400; 424/59; 516/53; 516/55; 516/83
(58) Field of Search ................................ 424/401, 400, 424/455, 59; 514/873, 937, 844, 846, 847, 848; 516/53, 55, 83

(56) References Cited

U.S. PATENT DOCUMENTS

| | | | |
|---|---|---|---|
| 5,207,998 A | 5/1993 | Robinson et al. | 424/59 |
| 5,420,118 A | 5/1995 | Alban et al. | 514/63 |
| 5,637,291 A | 6/1997 | Bara et al. | 424/59 |
| 5,643,555 A | 7/1997 | Collins et al. | 424/59 |
| 5,728,391 A | 3/1998 | Ikeya et al. | 424/401 |
| 5,804,167 A | 9/1998 | Schonrock et al. | 424/59 |
| 5,833,951 A | 11/1998 | Artz et al. | 424/47 |
| 5,849,318 A | 12/1998 | Imai et al. | 424/401 |
| 5,965,066 A | 10/1999 | Koch et al. | 252/589 |
| 6,013,247 A | 1/2000 | Bara et al. | 424/59 |

FOREIGN PATENT DOCUMENTS

| | | |
|---|---|---|
| EP | 0 539 251 A2 | 4/1993 |
| EP | 0 610 926 A1 | 8/1994 |
| EP | 0 680 746 A1 | 8/1995 |
| EP | 0 770 379 A2 | 5/1997 |
| EP | 0 823 249 A1 | 2/1998 |
| EP | 0 683 662 B1 | 6/1998 |

*Primary Examiner*—Michael G. Hartley
(74) *Attorney, Agent, or Firm*—Norris McLaughlin & Marcus PA

(57) ABSTRACT

Pickering emulsions, which are finely disperse systems of the water-in-oil or oil-in-water type, comprising
(1) an oil phase,
(2) a water phase,
(3) at least one type of microfine particles which
  a) have an average particle size of less than 200 nm, which
  b) display both hydrophilic and lipophilic properties, i.e. which have amphiphilic character, and are dispersible both in water and in oil and which
  c) have optionally been coated on the surface,
(4) at least one film former and
(5) at most 0.5% by weight of one or more emulsifiers.

17 Claims, No Drawings

EMULSIFIER-FREE FINELY DISPERSE SYSTEMS OF THE OIL-IN-WATER- AND WATER-IN-OIL- TYPE

This application is a divisional of application Ser. No. 09/396,560, filed on 15, Sep. 1999, now U.S. Pat. No. 6,709,662.

The present invention relates to emulsifier-free finely disperse systems of the oil-in-water and water-in-oil type, preferably as cosmetic or dermatological preparations.

Emulsions are generally taken to mean heterogeneous systems which consist of two liquids which are immiscible or have only limited miscibility with one another, which are usually referred to as phases. In an emulsion, one of the two liquids is dispersed in the form of very fine droplets in the other liquid.

If the two liquids are water and oil and if oil droplets are finely dispersed in water, then this is an oil-in-water emulsion (O/W emulsion, e.g. milk). The basic character of an O/W emulsion is defined by the water. In a water-in-oil emulsion (W/O emulsion, e.g. butter), the principle is reversed, the basic character here being determined by the oil.

In order to achieve permanent dispersion of one liquid in another, emulsions in the traditional sense require the addition of an interface-active substance (emulsifier). Emulsifiers have an amphiphilic molecular structure, consisting of a polar (hydrophilic) and a nonpolar (lipophilic) molecular moiety, which are spatially separate from one another. In simple emulsions, finely disperse droplets of one phase, surrounded by an emulsifier shell, (water droplets in W/O emulsions or lipid vesicles in O/W emulsions) are present in the second phase. Emulsifiers lower the interfacial tension between the phases by positioning themselves at the interface between two liquids. At the phase boundary, they form oil/water interfacial films, which prevent irreversible coalescence of the droplets. Emulsions are frequently stabilized using emulsifier mixtures.

Traditional emulsifiers can, depending on their hydrophilic molecular moiety, be divided into ionic (anionic, cationic and amphoteric) and nonionic:

The most well-known example of an anionic emulsifier is soap, which is usually the term used for the water-soluble sodium or potassium salts of saturated or unsaturated higher fatty acids.

Important examples of cationic emulsifiers are quaternary ammonium compounds.

The hydrophilic molecular moiety of nonionic emulsifiers frequently consists of glycerol, polyglycerol, sorbitans, carbohydrates and polyoxyethylene glycols, and, in most cases, is linked to the lipophilic molecular moiety via ester and ether bonds. The lipophilic molecular moiety usually consists of fatty alcohols, fatty acids or isofatty acids.

By varying the structure and the size of the polar and nonpolar molecular moiety, the lipophilicity and hydrophilicity of emulsifiers can be varied within wide limits.

A decisive factor for the stability of an emulsion is the correct choice of emulsifiers. The characteristics of all substances present in the system are to be taken into consideration here. In the case of, for example, skincare emulsions, polar oil components and, for example, UV filters lead to instability. As well as the emulsifiers, therefore, other stabilizers are also used which, for example, increase the viscosity of the emulsion and/or act as protective colloid.

Emulsions are an important type of product in the field of cosmetic and/or dermatological preparations.

Cosmetic preparations are essentially used for skin care. The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes). If this function becomes impaired, increased resorption of toxic or allergenic substances or attack by microorganisms may result, leading to toxic or allergic skin reactions.

Another aim of skin care is to compensate for the loss by the skin of lipids and water caused by daily washing. This is particularly important if the natural regeneration ability is inadequate. Furthermore, skincare products should protect against environmental influences, in particular against sun and wind, and delay skin ageing.

Cosmetic preparations are also used as deodorants. Such formulations are used to control body odour, which is produced when fresh perspiration, which is in itself odouriess, is decomposed by microorganisms.

Medicinal topical compositions usually comprise one or more medicaments in an effective concentration. For the sake of simplicity, in order to distinguish clearly between cosmetic and medicinal use and corresponding products, reference is made to the legal provisions in the Federal Republic of Germany (e.g. Cosmetics Directive, Foods and Drugs Act).

The use of customary emulsifiers in cosmetic or dermatological preparations is in itself acceptable. Nevertheless, emulsifiers, like ultimately any chemical substance, may in certain circumstances cause allergic reactions or reactions based on oversensitivity of the user.

For example, it is known that certain light dermatoses are triggered by certain emulsifiers, but also by various fats and simultaneous exposure to sunlight. Such light dermatoses are also called "Mallorca acne". There has thus been no lack of attempts to reduce the amount of customary emulsifiers to a minimum, in the ideal case even to zero.

A reduction in the required amount of emulsifier can, for example, be achieved by taking advantage of the fact that very finely divided solid particles have an additional stabilizing action. The solid substance accumulates at the oil/water phase boundary in the form of a layer, as a result of which coalescence of the disperse phases is prevented. It is not the chemical properties of the solid particles which are of fundamental importance here, but the surface properties.

Around 1910, Pickering prepared paraffin/water emulsions which were stabilized merely by the addition of various solids, such as basic copper sulphate, basic iron sulphate or other metal sulphates. This type of emulsion is thus also referred to as a Pickering emulsion.

The original forms of Pickering emulsions initially surfaced, as it were, as undesired secondary effects in a variety of industrial processes, such as, for example, in secondary oil recovery, the extraction of bitumen from tar sand and other separation processes involving two immiscible liquids and fine, dispersed solid particles. These are generally W/O emulsions which are stabilized by mineral solids. Accordingly, investigation of corresponding systems, such as, for example, the oil/water/soot or oil/water/slate dust systems was initially the focus of research activity.

Basic experiments have shown that one characteristic of a Pickering emulsion is that the solid particles are arranged at the interface between the two liquid phases, where they form, as it were, a mechanical barrier against the combining of the liquid droplets.

It is a relatively new technical development to use Pickering emulsions as a base for cosmetic or dermatological preparations.

One way of achieving solids stabilization in the sense of a pickering emulsion in a cosmetic or dermatological preparation is, according to May-Alert (*Pharmazie in unserer Zeit* [*Pharmacy in our time*], Vol. 15, 1986, No. 1, 1–7) for example, to use emulsifier mixtures which comprise both anionic and cationic surfactants. Since mixing anionic and cationic surfactants always results in the precipitation of insoluble, electroneutral compounds, deliberate precipitation of these neutral surfactants in the oil/water interface makes it possible to achieve additional solids stabilization.

European Laid-open Specification 0 686 391, moreover, describes emulsions of the water-in-oil type which are free from surface-active substances and are stabilized only by solids. Stabilization is achieved here using spherical polyalkylsilsesquioxane particles which have a diameter of from 100 nm up to 20 μm. These emulsions can be referred to as Pickering emulsions according to that mentioned above.

Pickering emulsions are stabilized by the use of suitable solids or pigments. However, the preparations of the prior art generally have the disadvantage that they are limited to a narrow field of application or a restricted choice of starting materials since they can only be stably formulated in this manner. For many areas of cosmetics (e.g. for the field of face care), Pickering emulsions of the prior art have unsatisfactory cosmetic properties.

In addition, when relevant preparations are applied to the skin, solids can leave behind a dry and sometimes dull impression. Even preparations with a pigment content of 1% by weight produce a dull feel on the skin following their application, which increases further with higher pigment concentrations. In some cases, therefore, pigment-containing preparations may not even be marketable since they are not accepted or are viewed negatively by the consumer.

The object was therefore to remedy the disadvantages of the prior art. In particular, the intention was to provide preparations which do not leave behind a dry or dull impression on the skin.

Furthermore, it was an object of the invention to develop cosmetic and dermatological bases for cosmetic and dermatological preparations which are characterized by good skin tolerability.

In addition, an object of the present invention was to provide products with the widest possible variety of applications. For example, the intention was to provide bases for preparation forms such as cleansing emulsions, facecare and bodycare preparations or deodorants, but also distinctly medicinal-pharmaceutical presentations, for example preparations against acne and other skin conditions.

It was surprising and in no way predictable by the person skilled in the art that Pickering emulsions, which are finely disperse systems of the water-in-oil or oil-in-water type, comprising (1) an oil phase,
(2) a water phase,
(3) at least one type of microfine particles which
   a) have an average particle size of less than 200 nm, which
   b) display both hydrophilic and lipophilic properties, i.e. which have amphiphilic character, and are dispersible both in water and in oil and which
   c) have optionally been coated on the surface,
(4) at least one film former and
(5) at most 0.5% by weight of one or more emulsifiers, overcome the disadvantages of the prior art.

According to the invention, it is particularly advantageous if the preparations comprise significantly less than 0.5% by weight of one or more emulsifiers or are even entirely free from emulsifiers.

The preparations according to the invention are extremely satisfactory preparations in every respect which surprisingly have excellent cosmetic properties, do not leave a dry or dull impression on the skin and are characterized by excellent skin tolerability. In addition, the preparations according to the invention have considerably higher stability than traditional Pickering emulsions and are therefore suitable in particular to serve as bases for preparation forms having diverse application purposes. Surprisingly, W/O Pickering emulsions in particular are significantly stabilized by a content of film formers.

In addition, it was surprising that preparations according to the invention which are present in the form of a sunscreen exhibit higher effectiveness than customary sunscreen formulations.

Although the prior art recognizes, in addition to Pickering emulsions, emulsifier-free, finely disperse cosmetic or dermatological preparations, which are generally referred to as hydrodispersions and which are dispersions of a liquid, semisolid or solid inner (discontinuous) lipid phase in an outer aqueous (continuous) phase, the prior art was unable to point the way to the present invention.

In the case of hydrodispersions of a liquid lipid phase in an outer aqueous phase, the stability can, for example, be ensured by constructing in the aqueous phase a gel structure in which the lipid droplets are stably suspended.

German Laid-open Specification 44 25 268 describes stable finely disperse, emulsifier-free cosmetic or dermatological preparations of the oil-in-water type which, in addition to an oil and a water phase, comprise one or more thickeners from the group of acrylic acid polymers, polysaccharides and the alkyl ethers thereof, where for these thickeners a lowering of the surface tension must not be measurable.

German Laid-open Specification 43 03 938 discloses cosmetic or dermatological light protection formulations based on similar hydrodispersions which are essentially free from emulsifiers, where inorganic micropigments are incorporated into the lipid phase of the hydrodispersion and serve as UV filter substances.

By contrast, for the purposes of the present invention, O/W Pickering emulsions are obtainable by firstly dispersing in the water phase amphiphilic particles according to the invention which are suitable for the preparation of O/W Pickering emulsions, and then combining the water phase with the fatty phase. By contrast, W/O Pickering emulsions according to the invention are obtainable by dispersing in the fatty phase amphiphilic particles according to the invention which are suitable for the preparation of W/O Pickering emulsions.

For the purposes of the present invention, film formers are substances of varying composition which are characterized by the following property: if a film former is dissolved in water or other suitable solvents, and the solution is then applied to the skin, after the solvent has evaporated, a film is formed which essentially has a protective function.

It is particularly advantageous to choose the film formers from the group of polymers based on polyvinylpyrrolidone (PVP)

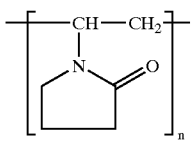

Particular preference is given to copolymers of polyvinylpyrrolidone, for example the PVP hexadecene copolymer and the PVP eicosene copolymer, which are obtainable under the trade names Antaron V216 and Antaron V220 from GAF Chemicals Corporation.

It is particularly advantageous to additionally stabilize W/O Pickering emulsions by the addition of copolymers of polyvinylpyrrolidone.

Likewise advantageous are other polymeric film formers, such as, for example, sodium polystyrenesulphonate, which is obtainable under the trade name Flexan 130 from National Starch and Chemical Corp., and/or polyisobutene, obtainable from Rewo under the trade name Rewopal PIB1000.

The total amount of one or more film formers is, in the finished cosmetic or dermatological W/O Pickering emulsions, advantageously chosen to be less than 10.0% by weight, preferably between 1.0 and 7.0% by weight, based on the total weight of the preparations, and in O/W Pickering emulsions advantageously chosen to be less than 20.0% by weight, preferably between 2.0 and 15.0% by weight, based on the total weight of the preparations.

It is also advantageous, but not obligatory, for the Pickering emulsions according to the invention to comprise other auxiliaries which can contribute to reducing or preventing a dull or dry feel on the skin following their application, where it is possible that the main purpose of these substances is a different one. Preferably, these substances are, for example, chosen from the group of unsymmetrically substituted s-triazine derivatives, cyclodextrins and polymeric moisturizers, it being possible for these substances to be present either individually or in a mixture.

The cosmetic properties of the Pickering emulsions according to the invention can additionally, for example, be further improved by using oils in the oil phase which have a viscosity of less than 30 mPa.s, in particular of less than 20 mPa.s (determined using a rheometer from Contraves (Rheomat 108E) at a shear gradient of 500/s and a temperature of 25° C.).

Microfine Particles:

The amphiphilic character of the microfine particles according to the invention is evident, for example, from the fact that they are dispersible both in water and in oil.

It is advantageous to choose the average particle diameter of the particles used to be between 1 nm and 200 nm, particularly advantageously between 5 nm and 100 nm.

It is also advantageous to choose the concentration of all amphiphilic particles according to the invention to be greater than 0.1% by weight, particularly advantageously between 0.1% by weight and 30% by weight, based on the total weight of the preparations.

For the purposes of the present invention, advantageous particles are all those which are suitable for stabilizing Pickering W/O or Pickering O/W emulsions. It is essentially insignificant for the present invention in which of the potentially naturally occurring modifications the particles are present.

To stabilize the Pickering emulsions, preference is given to using untreated, virtually pure pigment particles, in particular those which can be used as dyes in the food industry and/or as absorbers of UV radiation in sunscreens. Examples of advantageous pigments are the zinc oxide pigments available from Merck which are available under the trade names Zinkoxid neutral from Haarmann & Reimer or NanoX from Harcros Chemical Group.

For the purposes of the present invention, Pickering emulsions are likewise advantageously stabilized by inorganic pigments which have been surface-treated ("coated") to repel water, where at the same time the intention is to form or retain the amphiphilic character. This surface-treatment can consist in providing the pigments with a thin hydrophobic layer by processes known per se.

One such process, which is described below using titanium dioxide as an example, consists in, for example, producing the hydrophobic surface layer according to the following reaction $$n\ TiO_2 + m(RO)_3Si\text{—}R' \rightarrow n\ TiO_2(\text{surf.}).$$

n and m are arbitrary stoichiometric parameters, and R and R' are the desired organic radicals. Particularly advantageous are $TiO_2$ pigments, for example those coated with aluminium stearate, available under the trade name MT 100 T from TAYCA.

A further advantageous coating of the inorganic pigments consists of dimethylpolysiloxane (also: dimethicone), a mixture of completely methylated, linear siloxane polymers which are terminally blocked with trimethylsiloxy units. For the purposes of the present invention, particularly advantageous pigments are zinc oxide pigments which are coated in this way.

Also advantageous is a coating of the inorganic pigments with a mixture of dimethylpolysiloxane, in particular dimethylpolysiloxane having an average chain length of from 200 to 350 dimethylsiloxane units, and silica gel, which is also referred to as simethicone. It is particularly advantageous if the inorganic pigments have been additionally coated with aluminium hydroxide or hydrated aluminium oxide (also: alumina, CAS No.: 1333-84-2). Particularly advantageous are titanium dioxides which have been coated with simethicone and alumina, it being possible for the coating to also comprise water. One example thereof is the titanium dioxide available under the trade name Eusolex T2000 from Merck.

For the purposes of the present invention it is also advantageous to use a mixture of different pigment types either within a crystal, for example as mixed iron oxide, or by combination of two or more pigment types within a preparation.

The Pickering emulsions are also preferably stabilized by boron nitrides, for example by the boron nitrides listed below:

| Trade name | Available from |
| --- | --- |
| Boron Nitride Powder | Advanced Ceramics |
| Boron Nitride Powder | Sintec Keramik |
| Ceram Blanche | Kawasaki |
| HCST Boron Nitride | Stark |
| Tres BN ® | Carborundum |
| Wacker-Bornitrid BNP | Wacker-Chemie |

It is advantageous to choose the average particle diameter of the boron nitride particles used to be less than 20 μm, particularly advantageously less than 15 μm. For the purposes of the present invention, Pickering emulsions are likewise advantageously stabilized by boron nitride particles which have been surface-treated ("coated") to repel water, where at the same time the intention is to form or retain the amphiphilic character.

An advantageous coating of the boron nitride particles consists of dimethylpolysiloxane (dimethicone). The boron nitride particles treated with dimethicone and available from Carborundum under the trade name Très BN® UHP 1106 are advantageous, for example.

Also advantageous is a coating of the boron nitride particles with polymethylhydrogensiloxane, a linear polysiloxane which is also referred to as methicone. Advantageous boron nitride particles treated with methicone are, for example, those available from Carborundum under the trade name Très BN® UHP 1107.

It is also advantageous to stabilize the Pickering emulsions according to the invention using microfine polymer particles.

For the purposes of the present invention, examples of advantageous microfine polymer particles are polycarbonates, polyethers, polyethylenes, polypropylenes, polyvinyl chloride, polystyrene, polyamides, polyacrylates and the like.

Advantageous according to the invention are, for example, microfine polyamide particles which are available under the trade name SP-500 from TORAY. Also advantageous are polyamide 6 (also: nylon 6) and polyamide 12 (also: nylon 12) particles. Polyamide 6 is the polyamide formed from ε-aminocaproic acid (6-aminohexanoic acid) or ε-caprolactam [poly(ε-caprolactam)], and polyamide 12 is a poly(ε-laurolactam) from ε-laurolactam. For the purposes of the present invention, Orgasol® 1002 (polyamide 6) and Orgasol® 2002 (polyamide 12) from ELF ATOCHEM, for example, are advantageous.

Other advantageous polymer particles are microfine polymethacrylates. Such particles are available, for example, under the trade name POLYTRAP® from DOW CHEMICAL.

It is particularly advantageous, but not obligatory, if the microfine polymer particles used have been surface-coated. This surface-treatment can consist in providing the pigments with a thin hydrophilic layer by processes known per se. Advantageous coatings consist, for example, of $TiO_2$, $ZrO_2$ or also other polymers, such as, for example, polymethyl methacrylate.

Particularly advantageous microfine polymer particles for the purposes of the present invention are also obtainable by the process, described in U.S. Pat. No. 4,898,913, for the hydrophilic coating of hydrophobic polymer particles.

It is advantageous to choose the average particle diameter of the microfine polymer particles used to be less than 100 μm, particularly advantageously less than 50 μm. In this connection, it is essentially insignificant in which form (platelets, rods, spherules, etc.) the polymer particles used are present.

In addition, it is advantageous to stabilize the Pickering emulsions according to the invention using modified polysaccharides.

For the purposes of the present invention, modified polysaccharides are, for example, obtainable by reaction of starch with mono-, bi- or polyfunctional reagents or oxidizing agents in reactions which proceed in a largely polymer-analogous manner.

Such reactions are based essentially on modifications of the hydroxyl groups of the polyglucans by etherification, esterification or selective oxidation. This produces, for example, so-called starch ethers and starch esters of the general structural formula

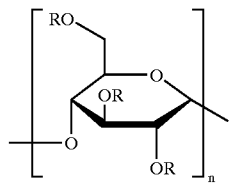

Structural formula (I)

in which R can, for example, be a hydrogen and/or an alkyl and/or an aralkyl radical (in the case of starch ethers) or a hydrogen and/or an organic and/or inorganic acid radical (in the case of starch esters). Starch ethers and starch esters are advantageous, modified polysaccharides for the purposes of the present invention.

Particularly advantageous starch ethers are, for example, those which are obtainable by etherification of starch with tetramethylolacetylenediurea and which are referred to as non-mucilaginous starch (nonswelling starch).

Also particularly advantageous are starch esters and salts thereof, for example the sodium and/or aluminium salts of half-esters of starch which have low degrees of substitution, in particular sodium starch n-octenyl succinate of the structural formula (II) in which R is characterized by the following structure

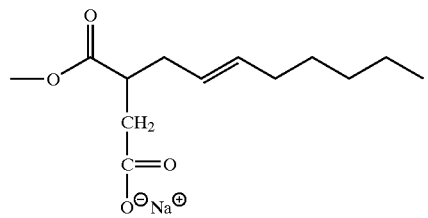

and which is available, for example, under the trade name Amiogum® 23 from CERESTAR, and aluminium starch octenyl succinates, in particular those available under the trade names Dry Flo® Elite LL and Dry Flo® PC from CERESTAR.

It is advantageous to choose the average particle diameter of the modified polysaccharide used to be less than 20 μm, particularly advantageously less than 15 μm.

The list of given modified polysaccharides which are able to stabilize Pickering emulsions according to the invention is of course not intended to be limiting. For the purposes of the present invention, modified polysaccharides are obtainable in a large number of ways known per se, both of a chemical and a physical nature.

The amphiphilic particles mentioned above are highly suitable both for stabilizing W/O Pickering emulsions and also for stabilizing O/W Pickering emulsions. Microfine particles according to the invention are given below which advantageously stabilize one of the two emulsion types W/O or O/W in particular.

W/O Pickering Emulsions:

The water phase proportion in the W/O Pickering emulsions according to the invention is preferably chosen from the range of from 0.5 to 75% by weight, based on the total weight of the formulations.

Also particularly advantageous for stabilizing W/O Pickering emulsions are magnesium silicates (also: talc), for example those available under the trade name Talkum Micron from Grolmann.

O/W Pickering Emulsions:

The fatty phase proportion of the O/W Pickering emulsions according to the invention is preferably chosen from the range from 0.5 to 75% by weight, based on the total weight of the formulations.

For the purposes of the present invention, untreated, virtually pure pigment particles are also particularly advantageous for stabilizing O/W Pickering emulsions, for example titanium dioxide pigments, in particular those which are obtainable under the trade name KRONOS® 1171 (TiO$_2$) from Kronos Titan.

For the purposes of the present invention, O/W Pickering emulsions are also particularly advantageously stabilized by metal oxide particles which have been coated with aluminium hydroxide and/or silicon dioxide. Advantageous variants are, for example, titanium dioxide particles which are obtainable under the name EUSOLEX® TA from Merck.

It is also advantageous, but not obligatory, to combine the microfine particles according to the invention with other amphiphilic particles which may or may not also be able to contribute to the stabilization of the Pickering emulsions.

Such particles are, for example, titanium dioxide pigments which have been coated with octylsilanol, and/or silicon dioxide particles which have been surface-treated to repel water. Suitable silicon dioxide particles are, for example, spherical polyalkylsilsesquioxane particles, as mentioned in European Laid-open Specification 0 686 391. Such polyalkylsilsesquioxane particles are available, for example, under the trade names Aerosil R972 and Aerosil 200V from Degussa. Suitable titanium dioxide particles are available under the trade name T805, also from Degussa.

The Pickering emulsions according to the invention can be used as bases for cosmetic or dermatological formulations. These can have the customary composition and be used, for example, for the treatment and care of the skin, as lipcare products, as deodorant products and as make-up products or make-up remover products in decorative cosmetics or as light protection preparations. For use, the cosmetic and dermatological preparations according to the invention are applied to the skin in sufficient amounts in the manner customary for cosmetics.

Accordingly, for the purposes of the present invention, cosmetic or topical dermatological compositions may, depending on their structure, be used, for example, as skin-protection creams, cleansing milks, sunscreen lotions, nourishing creams, day creams or night creams, etc. In some instances, it is possible and advantageous to use the compositions according to the invention as bases for pharmaceutical formulations.

The cosmetic and dermatological preparations according to the invention can comprise cosmetic auxiliaries, as are customarily used in such preparations, e.g. preservatives, bactericides, perfumes, antifoams, dyes, pigments which have a colouring effect, further thickeners, emollients, moisturizers and/or humectants, fats, oils, waxes and other customary constituents of a cosmetic or dermatological formulation, such as alcohols, polyols, polymers, foam stabilizers, electrolytes, organic solvents or silicone derivatives.

Pickering emulsions according to the invention may also comprise thickeners to improve the tactile properties of the emulsion.

In particular, the Pickering emulsions according to the invention may also comprise antioxidants. According to the invention, favourable antioxidants which can be used are any antioxidants suitable or conventional for cosmetic and/or dermatological applications.

The antioxidants are advantageously chosen from the group consisting of amino acids (e.g. glycine, histidine, tyrosine, tryptophan) and derivatives thereof, imidazoles, (e.g. urocanic acid) and derivatives thereof, peptides, such as D,L-camosine, D-camosine, L-camosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and the salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, α-glycosylrutin, ferulic acid, furfurylideneglucitol, carnosine, butylated hydroxytoluene, butylated hydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active substances which are suitable according to the invention.

The amount of the abovementioned antioxidants (one or more compounds) in the preparations according to the invention is preferably from 0.001 to 30% by weight, particularly preferably from 0.05–20% by weight, in particular 1–10% by weight, based on the total weight of the preparation.

If vitamin E and/or derivatives thereof are used as the antioxidant or antioxidants, their respective concentrations are advantageously chosen from the range of 0.001–10% by weight, based on the total weight of the formulation.

If vitamin A or vitamin A derivatives or carotenes or derivatives thereof are used as the antioxidant or antioxidants, their respective concentrations are advantageously chosen from the range of 0.001–10% by weight, based on the total weight of the formulation.

Cosmetic and dermatological preparations which are in the form of a sunscreen are also favourable. These preferably comprise at least one UV-A filter substance and/or at least one UV-B filter substance and/or at least one further inorganic pigment selected from the group consisting of the oxides of iron, zirconium, silicon, manganese, aluminium, cerium and mixtures thereof and also modifications in which the oxides are the active agents.

For the purposes of the present invention, it is, however, also advantageous to provide such cosmetic and dermatological preparations whose main purpose is not protection against sunlight, but which nevertheless comprise substances which protect against UV. For example, UV-A and UV-B filter substances are commonly incorporated into day creams.

The preparations according to the invention can advantageously comprise substances which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the whole of ultraviolet radiation.

If the emulsions according to the invention comprise UV-B filter substances, the latter may be oil-soluble or water-soluble. Examples of oil-soluble UV-B filters which are advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate, derivatives of benzophenone, preferably 2-hydroxy4-methoxybenzophenone, 2-hydroxy4-methoxy4'-methylbenzophenone, 2,2'-dihydroxy-4-methoxybenzophenone;

esters of benzmalonic acid, preferably di(2-ethylhexyl) 4-methoxybenzalmalonate, triazine derivatives which are symmetrical with regard to the $C_3$ axis of the triazine parent substance, preferably tris(2-ethylhexyl) 4,4',4"-(1,3,5-triazine-2,4,6-triyltriimino)trisbenzoate, benzotriazole derivatives, preferably 2,2'-methylenebis(6-(2H-benzotriazol-2-yl)4-(1,1,3,3,-tetramethylbutyl)phenol)

and UV filters bonded to polymers.

Examples of advantageous water-soluble UV-B filters are:

salts of 2-phenylbenzimidazole-5-sulphonic acid, such as its sodium, potassium or triethanolammonium salts, and the sulphonic acid itself;

sulphonic acid derivatives of benzophenones, preferably 2-hydroxy4-methoxybenzophenone-5-sulphonic acid and salts thereof;

sulphonic acid derivates of 3-benzylidenecamphor, such as, for example, 4-(2-oxo-3-bornylidenemethyl)benzenesulphonic acid, 2-methyl-5-(2-oxo-3-bornylidene-methyl)sulphonic acid and salts thereof.

The list of UV-B filters mentioned which can be used in the Pickering emulsions according to the invention is of course not intended to be limiting.

It can also be advantageous to use UV-A filters in Pickering emulsions according to the invention which have hitherto customarily been present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)-propane-1,3-dione.

Other advantageous UV-A filter substances are phenylene-1,4-bis(2-benzimidazyl)3,3'-5,5'-tetrasulphonic acid:

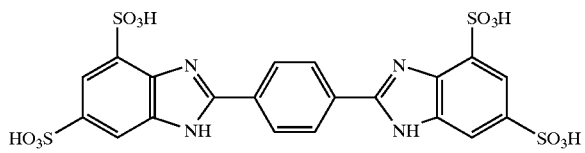

and its salts, particularly the corresponding sodium, potassium or triethanolammonium salts, in particular the bis-sodium salt of phenylene-1,4-bis(2-benzimidazyl)-3,3'-5,5'-tetrasulphonic acid:

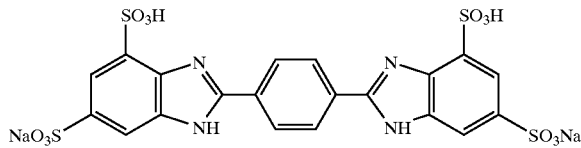

and 1,4-di(2-oxo-10-sulfo-3-bornylidenemethyl)benzene and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulphonic acid) and is characterized by the following structure:

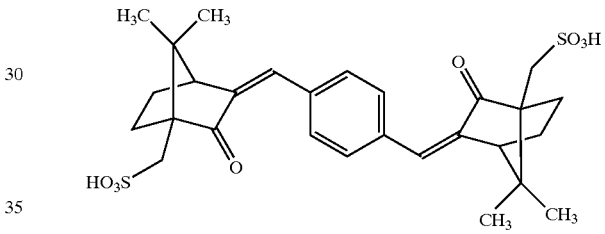

Preparations which comprise UV-A filters are also provided by the invention. The amounts which can be used are those used for the UV-B combination.

Preparations according to the invention can also be advantageously used as bases for cosmetic deodorants and antiperspirants, so that a particular embodiment of the present invention relates to Pickering emulsions as bases for cosmetic deodorants.

Cosmetic deodorants are used to control body odour which arises when fresh perspiration, which is in itself odourless, is decomposed by microorganisms. Customary cosmetic deodorants are based on various modes of action.

In antiperspirants, astringents, mainly aluminium salts, such as aluminium hydroxychloride (aluminium chlorohydrate), reduce the formation of perspiration.

The use of antimicrobial substances in cosmetic deodorants can reduce the bacterial flora of the skin. In an ideal situation, only the microorganisms which cause the odour should be effectively reduced. The flow of perspiration itself is not influenced as a result, and in ideal circumstances, only microbial decomposition of perspiration is stopped temporarily.

The combination of astringents and antimicrobial active substances in one and the same composition is also common.

All active ingredients common for deodorants or antiperspirants can advantageously be used, for example odour concealers, such as customary perfume constituents, odour absorbers, for example the phyllosilicates described in Laid-open Patent Specification DE 40 09 347, of these in particular montmorillonite, kaolinite, illite, beidellite, nontronite, saponite, hectorite, bentonite, smectite, and also, for example, zinc salts of ricinoleic acid. Antibacterial agents are also suitable to be incorporated into the novel W/O emulsion sticks. Advantageous substances are, for example, 2,4,4'-trichloro-2'-hydroxy diphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol) and also the active ingredients or active ingredient combinations described in the Laid-open Patent Specifications DE-A-37 40 186, DE-A-39 38 140, DE-A-42 04 321, DE-A-42 29 707, DE-A-43 09 372, DE-A-44 11 664, DE-A-195 41 967, DE-A-195 43 695, DE-A-195 43 696, DE-A-195 47 160, DE-A-196 02 108, DE-A-196 02 110, DE-A-196 02 111, DE-A-196 31 003, DE-A-196 31 004 and DE-A-196 34 019, and the Patent Specifications DE-42 29 737, DE-42 37 081, DE-43 24 219, DE-44 29 467, DE-44 23 410 and DE-195 16 705. Sodium hydrogencarbonate can also be used advantageously.

The list of specified active ingredients and active ingredient combinations is of course not intended to be limiting.

The amount of antiperspirant active ingredients or deodorants (one or more compounds) in the preparations is preferably from 0.01 to 30% by weight, particularly preferably from 0.1 to 20% by weight, in particular 1–10% by weight, based on the total weight of the preparation.

The examples below serve to illustrate the present invention without limiting it. The numerical values in the examples are percentages by weight, based on the total weight of the respective preparations.

| | Examples: | | | | | |
|---|---|---|---|---|---|---|
| | 1 W/O | 2 W/O | 3 W/O | 4 O/W | 5 O/W | 6 O/W |
| Titanium dioxide (Eusolex T2000) | 2 | 4 | 6 | 3 | 5 | 2 |
| Zinc oxide | 5 | | 4 | | | 4 |
| Titanium dioxide (Titandioxid T805) | | | 2 | | | |
| Silica (Aerosil R972) | | 1 | 0.5 | | | |
| Talc (Talkum Micron) | | 0.5 | | | | |
| Boron nitride | | 2 | | | | |
| Sodium corn starch n-octenyl succinate | | | | 0.5 | | 1 |
| Hydroxystearyl hydroxystearate (Elfacos C26) | 2 | | 2 | | | |
| C$_{20-40}$-alkyl stearate (Kesterwachs K82) | 1 | 1 | | | | |
| C$_{16-38}$-alkylhydroxystearolyl stearate (Kesterwachs K80P) | | 2 | | | | |
| Behenoxydimethicone (Abil Wax 2440) | | | 5 | | 5 | |
| Polyisobutene (Rewopal PIB 1000) | 5 | | 2 | | | 5 |
| PVP Hexadecene copolymer (Antaron V216) | | 2 | 2 | | 5 | |
| Sodium polystyrenesulphonate (Flexan 130) | | | | 2 | | |
| Caprylic/capric triglyceride | 5 | 5 | 5 | 10 | 15 | 15 |
| Octyldodecanol | 5 | | 5 | 15 | | 15 |
| Mineral oil | 10 | | | 10 | | 10 |
| Butylene glycol caprylate/caprate | 10 | | 5 | | 20 | 7 |
| C$_{12-15}$-alkyl benzoate | | 10 | 10 | 5 | 15 | |
| Dimethicone | 2 | 2 | 1 | | 2 | |
| Dicaprylyl ether (Cetiol OE) | | | 5 | 5 | | 10 |
| Hydrogenated polyisobutene (Polysynlan) | 2 | 10 | | | | |
| Isohexadecane | 3 | | | 5 | | |
| Methylbenzylidenecamphor | | 3 | | | 4 | |
| Octyltriazone | | 1 | | | 4 | |
| Dibenzoylmethane | | 2 | | | 2 | |
| Dioctylbutamidotriazone (UVASORB HEB) | | 2 | | | | |
| Preservative | 0.5 | 0.5 | 0.5 | 0.5 | 0.5 | 0.5 |
| Glycerol | 5 | 10 | 3 | 5 | 5 | 5 |
| Biosaccharide gel (Fucogel 1000) | | | 5 | | | |
| Hyaluronic acid | | | | | 0.5 | |
| NaCl | 1 | | 1 | | | |
| MgSO$_4$ | | 0.5 | | | | |
| Phenylbenzimidazolesulphonic acid | | 1 | | | 2 | |
| Carbomer (Carbopol 981) | | | | 0.1 | | |
| Xanthan gum | | | | 0.3 | | |
| Cellulose gum (Natrosol Plus 330 CS) | | | 0.1 | | | |
| NaOH 45% strength solution in water | | 0.3 | | 0.1 | 0.7 | |
| EDTA solution | | 1 | | | 1 | |
| Water | ad 100 | ad 100 | ad 100 | ad 100 | ad 100 | ad 100 |

What is claimed is:

1. A Pickering emulsion, said Pickering emulsion being a finely dispersed water-in-oil or oil-in-water system, said Pickering emulsion comprising:
    a) an oil phase comprising at least one wax and/or at least one oil thickener;
    b) an aqueous phase;
    c) microfine particles, said microfine particles being metal oxides:
        i) having an average particle size of less than 200 nm;
        ii) being dispersible both in water and in oil; and
        iii) having both hydrophilic and lipophilic properties resulting in amphiphilic character;
    d) at least one film former; and
    e) at most 0.5% by weight of one or more emulsifiers.

2. Pickering emulsion according to claim 1, are emulsifier-free.

3. Pickering emulsion according to claim 1, the content of the particles used is between 0.1% by weight and 30% by weight, based on the total weight of the preparations.

4. Pickering emulsion according to claim 1, wherein the particle diameter of the particles used is between 5 nm and 100 nm.

5. Pickering emulsion according to claim 1, the particles have been surface-treated to repel water, where the amphiphilic character of the particles is formed or retained.

6. W/O Pickering emulsion according to claim 1, the total amount of one or more film formers in the emulsion is chosen to be less than 10% by weight based on the total weight of the emulsion.

7. W/O Pickering emulsion according to claim 6, wherein the total amount of one or more film formers in the emulsion is between 1.0 and 7.0% by weight, based on the total weight of the emulsion.

8. W/O Pickering emulsion according to claim 1, the total amount of one or more film formers is chosen to be less than 20.0% by weight based on the total weight of the emulsion.

9. Pickering emulsion according to claim 8, wherein the total amount of one or more film formers in the emulsion is between 2.0 and 15.0% by weight, based on the total weight of the emulsion.

10. Pickering emulsion according to claim 1, wherein the film former(s) is/are selected from the group of polyvinylpyrrolidone (PVP) polymers.

11. Pickering emulsion according to claim 10, wherein the film former(s) is/are selected from the group of polyvinylpyrrolidone copolymers.

12. Pickering emulsion according to claim 1, wherein the film former(s) is/are selected from the group consisting of PVP hexadecene copolymer, PVP eicosene copolymer, sodium polystyrenesulphonate and polyisobutene.

13. A method of providing skin care, said method comprising applying to skin an emulsion according to any one of claims 1–12.

14. A method for stabilizing a cosmetic or dermatological Pickering emulsion comprising of:
 a) an oil phase comprising at least one wax and/or at least one oil thickener;
 b) an aqueous phase;
 c) microfine particles, said microfine particles being metal oxides:
  i) having an average particle size of less than 200 nm;
  ii) being dispersible both in water and in oil; and
  iii) having both hydrophilic and lipophilic properties resulting in amphiphilic character; and
 d) at most 0.5% by weight of one or more emulsifiers,
which consists of adding at least one film former to said Pickering emulsion.

15. The method of claim 14 wherein said at least one film former is selected from the group of polyvinylpyrrolidone (PVP) polymers.

16. The method of claim 15 wherein said at least one film former is selected from the group of polyvinylpyrrolidone copolymers.

17. The method of claim 16 wherein said at least one film former is selected from the group consisting of PVP hexadecene copolymer, PVP eicosene copolymer, sodium polystyrenesulphonate and polyisobutene.

* * * * *

UNITED STATES PATENT AND TRADEMARK OFFICE
CERTIFICATE OF CORRECTION

PATENT NO. : 6,838,088 B2
APPLICATION NO. : 10/081779
DATED : January 4, 2005
INVENTOR(S) : Gers-Barlag et al.

It is certified that error appears in the above-identified patent and that said Letters Patent is hereby corrected as shown below:

Column 10, Line 2, "D,L-camosine, D-camosine, L-camosine" should read -- D,L-carnosine, D-carnosine, L-carnosine --

Column 11, Line 28, "preferably 2-hydroxy4-" should read -- preferably 2-hydroxy-4- --

Column 11, Line 29, "2-hydroxy4-methoxy4'-" should read -- 2-hydroxy-4-methoxy-4'- --

Column 11, Line 40, "(2H-benzotriazol-2-yl)4-" should read -- (2H-benzotriazol-2-yl)-4- --

Column 11, Line 66, "(2-benzimidazyl)3,3'-5,5'-tetrasulphonic" should read -- (2-benzimidazyl)-3,3'-5,5'-tetrasulphonic --

Column 15, Line 20, "W/O Pickering" should read -- O/W Pickering --

Column 15, Line 23, "Pickering emulsion" should read -- O/W Pickering emulsion --

Signed and Sealed this

Twenty-seventh Day of April, 2010

David J. Kappos
*Director of the United States Patent and Trademark Office*